United States Patent [19]
Brimhall et al.

[11] Patent Number: 5,810,780
[45] Date of Patent: Sep. 22, 1998

[54] MULTIPLE CROSS SECTION NEEDLE AND ELASTIC PLUG ASSEMBLY FOR A MEDICAL DEVICE

[75] Inventors: Greg L. Brimhall, West Jordan; Christopher P. Steinman, Sandy; Stephen L. Thoresen, Orem, all of Utah

[73] Assignee: Becton Dickinson and Company, Franklin Lakes, N.J.

[21] Appl. No.: 645,548

[22] Filed: May 10, 1996

[51] Int. Cl.$^6$ ................................................ A61M 5/178
[52] U.S. Cl. .......................... 604/167; 604/164; 604/264; 604/272
[58] Field of Search ................................. 604/161, 239, 604/264, 272, 273, 164, 158, 280, 166, 168, 167, 256

[56] References Cited

U.S. PATENT DOCUMENTS

| | | |
|---|---|---|
| 1,147,408 | 7/1915 | Kells . |
| 2,748,769 | 6/1956 | Huber ...................... 128/221 |
| 2,828,744 | 4/1958 | Hirsch et al. . |
| 2,899,959 | 8/1959 | Ginsburg . |
| 2,899,960 | 8/1959 | Ginsburg . |
| 3,766,916 | 10/1973 | Moorehead et al. ............. 128/214.4 |
| 4,531,937 | 7/1985 | Yates ............................ 604/53 |
| 4,610,671 | 9/1986 | Luther ........................ 604/168 |
| 4,735,614 | 4/1988 | Yapp et al. .................. 604/165 |
| 4,781,691 | 11/1988 | Gross ......................... 604/164 |
| 4,791,937 | 12/1988 | Wang .......................... 128/752 |
| 4,966,587 | 10/1990 | Baumgart .................... 604/164 |
| 5,053,014 | 10/1991 | Van Heugten ............... 604/167 |
| 5,084,023 | 1/1992 | Lemieux ..................... 604/167 |
| 5,085,648 | 2/1992 | Purdy et al. ................. 604/198 |
| 5,163,913 | 11/1992 | Rantanen-Lee et al. ......... 604/177 |
| 5,167,635 | 12/1992 | Haber et al. ................. 604/164 |
| 5,267,971 | 12/1993 | Brimhall ..................... 604/177 |
| 5,330,433 | 7/1994 | Fonger et al. ................ 604/164 |
| 5,498,247 | 3/1996 | Brimhall ..................... 604/244 |
| 5,558,651 | 9/1996 | Crawford et al. ............. 604/263 |
| 5,630,802 | 5/1997 | Moellmann et al. ........... 604/164 |

FOREIGN PATENT DOCUMENTS

| | | |
|---|---|---|
| 0 139 091 A1 | 5/1985 | European Pat. Off. . |
| 44 34 569 A1 | 3/1995 | Germany . |
| 2088215 | 11/1984 | United Kingdom ............ A61M 5/00 |

Primary Examiner—Corrine M. McDermott
Assistant Examiner—Cris L. Rodriguez
Attorney, Agent, or Firm—Eric M. Lee

[57] ABSTRACT

The assembly of this invention comprises an elastic plug that is retained in a medical device, such as a catheter. A needle having a distal portion and a proximal portion resides in the elastic plug. The proximal portion has a different cross-section than the distal portion. In one embodiment, the cross-section of the proximal portion is smaller than the distal portion. Upon removal of the needle from the catheter and the elastic plug, the space in the elastic plug that had been occupied by the proximal portion of the needle is closed to effectively achieve the sealing function of the plug. The needle may include one or more notches in fluid communication with the needle lumen. One notch is preferably located at the juncture between the proximal portion and the distal portion of the needle to facilitate the blood flow between the needle and the catheter for better visualization of blood flashback by the clinician.

10 Claims, 6 Drawing Sheets

MULTIPLE CROSS SECTION NEEDLE AND ELASTIC PLUG ASSEMBLY FOR A MEDICAL DEVICE

BACKGROUND OF THE INVENTION

This invention relates to a needle having at least two different cross-sections along its length and an elastic plug assembly for use in a medical device, such as an intravenous (IV) catheter. Although this invention will be discussed in connection with its application to an IV catheter, it is to be understood that this invention may be used in conjunction with other medical devices which employ a needle that passes through an elastic plug.

The most common type of catheter is an over-the-needle catheter. As its name implies, an over-the-needle catheter is mounted over an introducer needle having a sharp distal tip. With the sharp distal tip of the introducer needle extending beyond the distal tip of the catheter, the assembly is inserted through the patient's skin into a vein. Once placement of the assembly in the vein is verified by flashback of blood, the needle is withdrawn from the catheter while the catheter is advanced in place in the patient's vein. The proximal end of the catheter typically has a hub that is designed to be connectable to an IV fluid supply line or other medical device such as a syringe or valve.

Although typical catheter and introducer needle assemblies generally perform their functions satisfactorily, they do have certain drawbacks. For example, once the needle is withdrawn from the catheter, the catheter becomes a source of blood spillage until the proximal end of the catheter is connected to an IV fluid supply line or other medical device. One way to avoid this blood leakage is by using an elastic plug to seal the proximal end of the catheter. Prior art plugs generally perform well. However, it has been found that the material of these plugs may take a set to the needle, particularly if the needle remains in the plug for a considerable period of time while the assembly is in inventory before use. Thus, when the needle is removed from the plug, a small hole in the plug remains where the needle had been. Such a small hole will place the venous system of the patient in communication with ambient atmosphere. This can result in blood leakage or provide a path for microbial infection to the patient.

In addition, in order to determine whether the venipuncture has been successful, the clinician must observe flashback of blood. In typical catheters a flashback chamber is located at the proximal end of the needle. Thus during venipuncture the clinician must divert his attention away from the insertion site at the distal end of the assembly to the proximal end of the assembly. This is undesirable. In an attempt to obviate this problem some catheters provide the needle with a notch adjacent to its distal end. In this manner, flashback of blood can be observed in the annular space between the needle and the catheter. Unfortunately, this arrangement is inadequate because many times blood flow is insufficient in the annular space between the needle and catheter for the clinician to make a clear determination that the venipuncture has been successful.

SUMMARY OF THE INVENTION

It is therefore an object of this invention to provide a needle and catheter assembly where the catheter will not leak blood after the needle has been withdrawn from the catheter.

It is another object of this invention to provide a needle and catheter assembly where the catheter will not provide a path for microbial infection to the patient after the needle has been withdrawn from the catheter.

It is still another object of this invention to provide a needle and catheter assembly that will provide a clear indication, adjacent to the distal end of the assembly, that a successful venipuncture has been made.

The needle and elastic plug assembly of this invention includes a needle having at least two different cross-sections along its length. Preferably, the proximal portion of the needle has a smaller cross-section than the distal portion of the needle. When the needle is properly located in the catheter so the sharp distal tip of the needle extends past the distal end of the catheter, the smaller cross-section proximal portion of the needle resides in an elastic plug that is held in the catheter hub. The elastic plug may be held in compression by the catheter hub. Having the smaller cross-section proximal portion of the needle reside in the elastic plug minimizes the possibility that the elastic plug will take a set around the needle or, at a minimum, minimizes the size of the set. Once the needle is removed from the catheter, the elastic plug will minimize leakage of blood from the catheter and minimize the chance of infection to the patient. In addition, since the elastic plug is subject to radial compression, any hole will tend to be forced closed by the compressive force.

The needle may have one or more notches therein to provide a path for the flashback of blood outside of the needle in the annular space with the catheter. In this way, visualization of the flashback of blood may be made when the blood flows in the annular space between the catheter and the needle or along a distally mounted extension tube extending from the catheter hub. Preferably, the needle has a notch in a sidewall adjacent to the point where the needle transitions to its smaller cross-section proximal portion. This configuration facilitates blood flow out of the notch. In addition, the smaller cross-section proximal portion of the needle ensures that there is an annular flow path between the needle and the catheter for the flashback of blood. This annular flow path results in greater blood flow between the needle and catheter and facilitates blood visualization so the clinician will know immediately if the venipuncture has been successful. Although the proximal portion of the needle may have a smaller cross-section than the distal portion, the proximal portion may also have a different cross-section than the distal portion. This different cross-section should be such so as to ensure an improved flow path for blood in the annular space between the needle and the catheter.

BRIEF DESCRIPTION OF THE DRAWINGS

The above and other objects and advantages of the invention will be apparent upon consideration of the drawings and the following detailed description. The preferred embodiments are illustrated in the drawings in which like reference numerals refer to like elements and in which.

DETAILED DESCRIPTION OF THE PREFERRED EMBODIMENT

The multiple cross-section needle and elastic plug assembly of this invention can be used with any device which requires a needle to pass through an elastic plug that must reseal when the needle is removed. However, this invention has special application to IV catheters, especially the catheter shown in FIG. 1.

Figure 1:
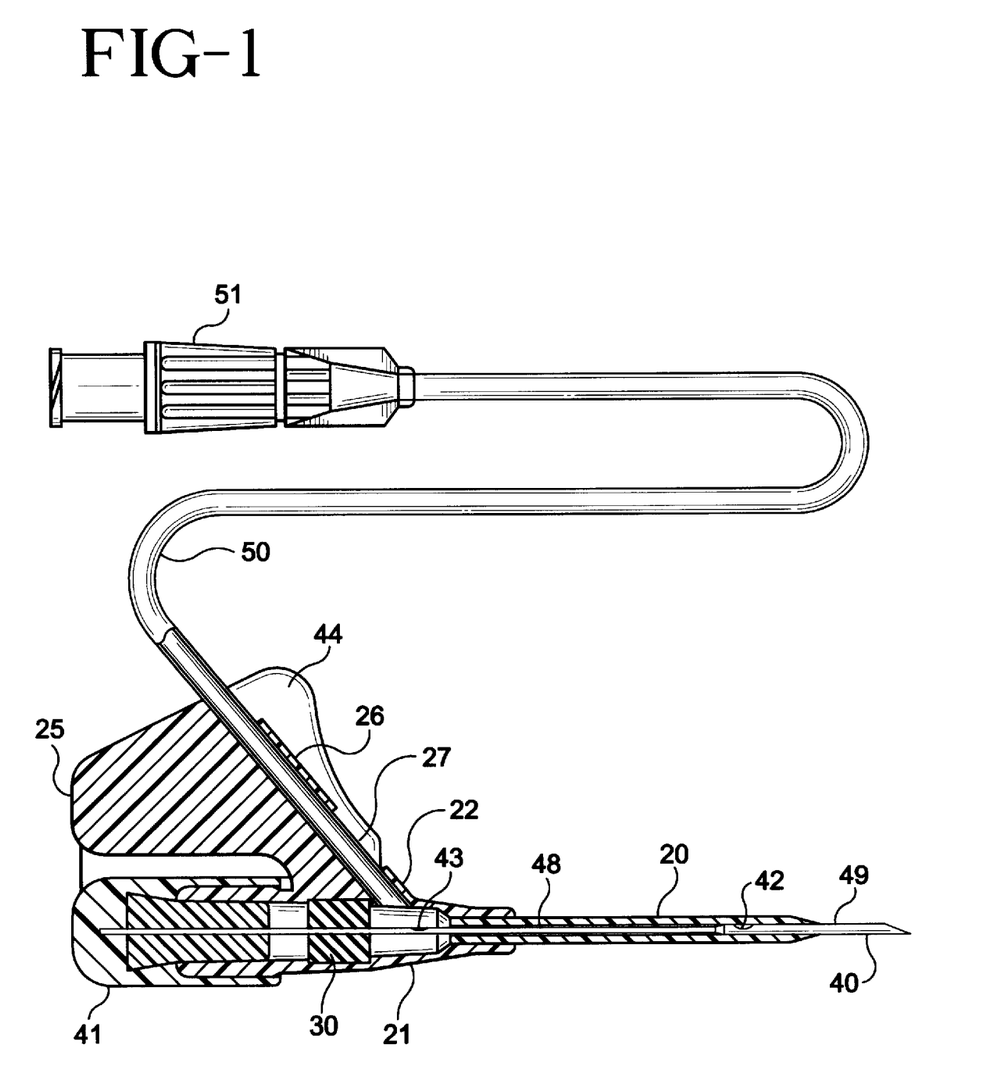
FIG. 1 is a side elevation view partially in cross-section of a catheter and introducer needle assembly including the needle and elastic plug assembly of this invention.

The catheter and introducer needle assembly shown in FIG. 1 includes a catheter 20 affixed to a catheter hub 21 and a needle 40 affixed to a needle hub 41. Catheter hub 21 includes a side port 22 which has an extension tube 50 connected thereto located toward the distal portion of catheter hub 21. This catheter is described in detail in (P-2962) U.S. patent application Ser. No. 08/405,324, the disclosure of which is hereby incorporated by reference.

The proximal end of extension tube 50 includes a standard luer lock adaptor 51 to allow the connection of an IV fluid supply line to extension tube 50. Such an IV fluid supply line can be connected to extension tube 50 prior to insertion of catheter 20 into a patient. Side port 22 is in fluid communication with the lumen of catheter 20 so that fluid infused through extension tube 50 will pass into the patient once catheter 20 is properly positioned in the patient. Conversely, blood exiting a patient's vein through catheter 20 can travel through extension tube 50.

Catheter hub 21 also includes a wing 25 that extends radially from catheter hub 21. Wing 25 is generally aligned with the longitudinal axis of catheter 20. Wing 25 should be large enough to be grasped easily by a clinician. The distal end of wing 25 defines a tubular member 26 which preferably does not extend the entire length of the distal end of wing 25. Extension tube 50 fits through tubular member 26 into communication with side port 22. The space between side port 22 and tubular member 26 defines a window 27 that allows the clinician to observe the distal portion of extension tube 50. At least that part of extension tube 50 that extends past window 27 is formed from polyvinyl chloride so that it is translucent or transparent in window 27. Of course, other suitable translucent or transparent materials could also be used to form that portion of extension tube 50. In this manner, flashback of blood can be observed in window 27 once needle 40 has entered a patient's vein. Window 27 is not necessary where tubular member 26 is made of a clear material such as polycarbonate. In such a case, flashback of blood through extension tube 50 can be seen through tubular member 26.

Figure 4:
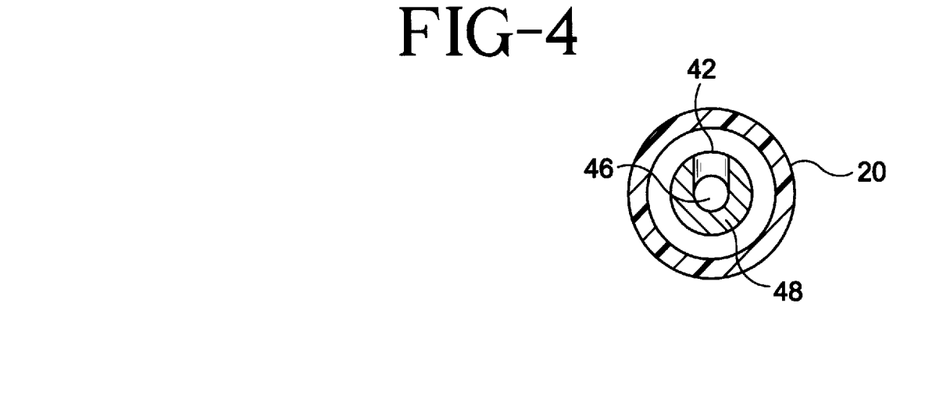
FIG. 4 is a cross-sectional view taken along line 4—4 of FIG. 3.
Figure 8:
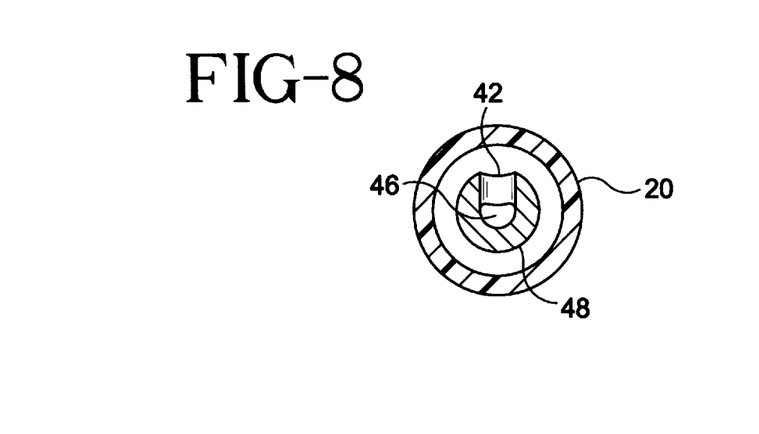
FIG. 8 is a cross-sectional view taken along line 8—8 of FIG. 7.
Figure 10:
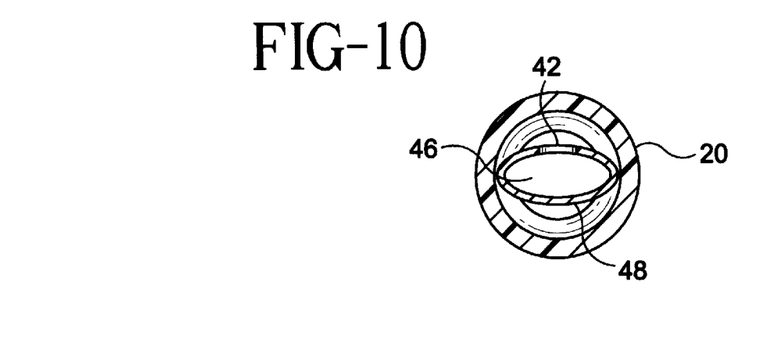
FIG. 10 is a cross-sectional view taken along line 10—10 of FIG. 9.

Needle 40 has its proximal end connected to needle hub 41. Radially extending fin 44 is formed on needle hub 41 and is generally longitudinally aligned with needle 40. Needle 40 includes a distal portion 49 having a first cross-section and a proximal portion 48 having a second cross-section. For example, proximal portion 48 may have a reduced cross-section as compared to distal portion 49. See FIGS. 4, 6 and 8. In such a case proximal portion 48 should have a diameter that is one gauge size smaller than the diameter of distal portion 49. Alternatively, the different cross-section of proximal portion 48 could have a comparable cross-sectional area to distal portion 49. See FIG. 10. In both of these cases, the key consideration is for proximal portion 48 to have a different cross-section than distal portion 49 in order to define a space between proximal portion 48 and catheter 20 to provide a fluid flow space therebetween. Distal portion 49 should have a standard cross-section so the distal tip of catheter 20 can tightly grip distal portion 49 to aid insertion of catheter 20 into a patient.

Figure 2:
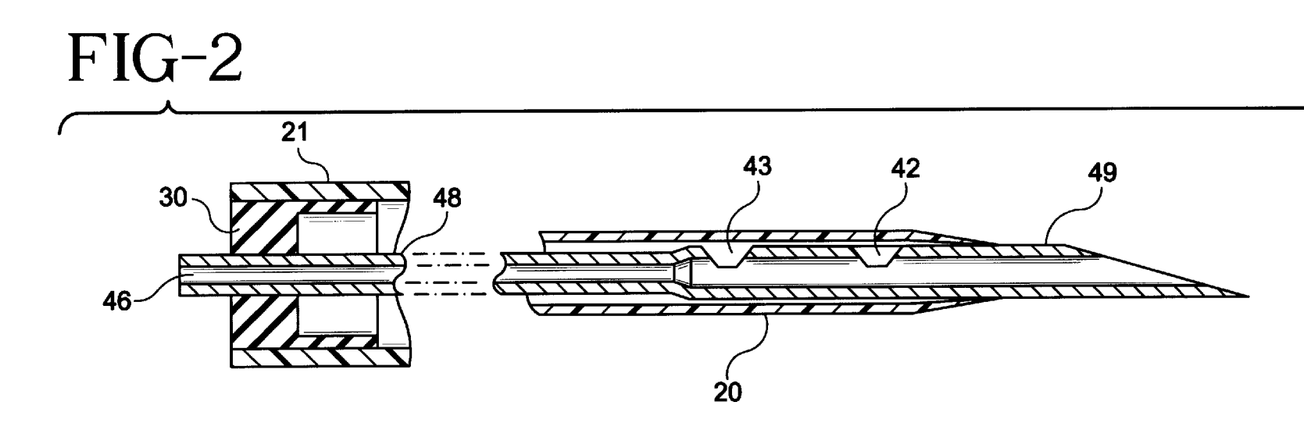
FIG. 2 is an enlarged cross-sectional view of one embodiment of the needle and elastic plug of this invention.
Figure 2A:
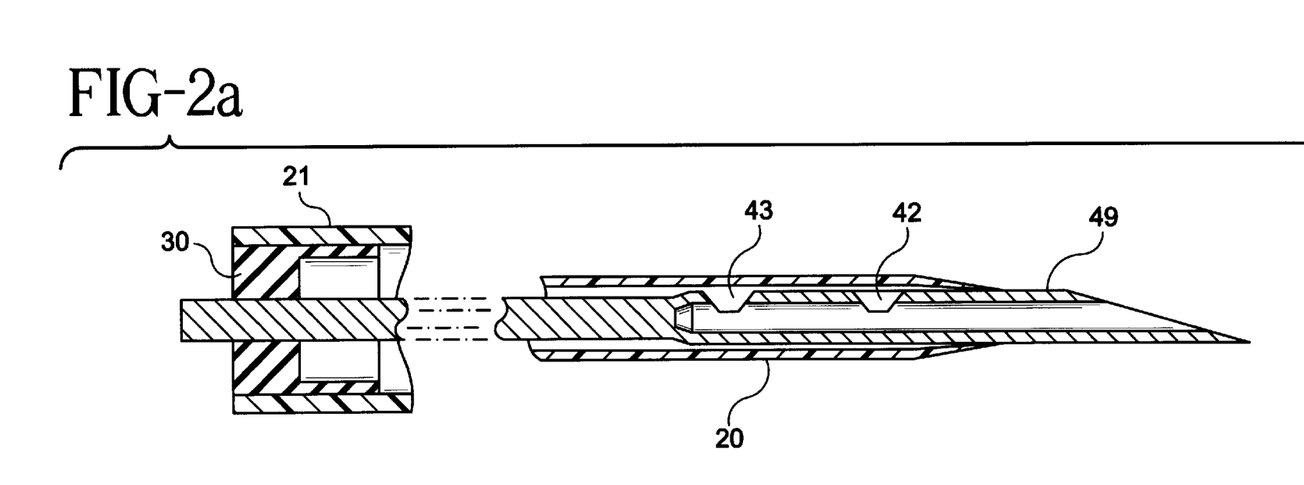
FIG. 2a is an enlarged cross-sectional view of one embodiment of the needle and elastic plug of this invention wherein the proximal portion of the needle is occluded.
Figure 3:
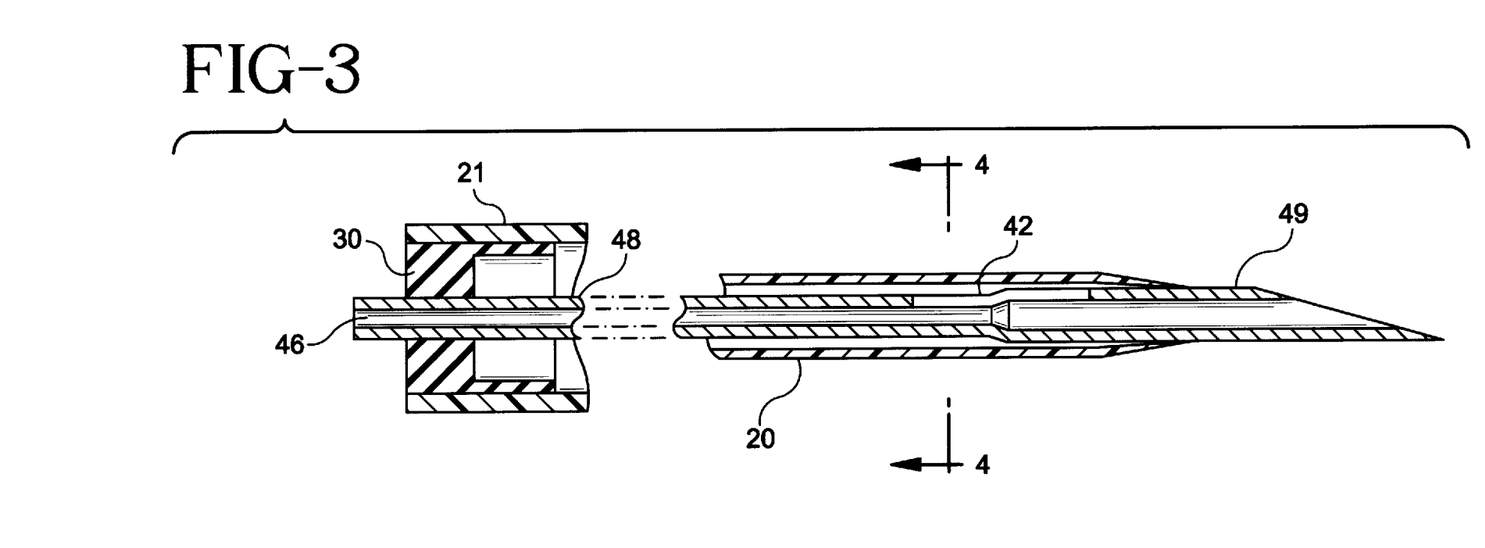
FIG. 3 is an enlarged cross-sectional view of another embodiment of the needle and elastic plug of this invention.

Proximal portion 48 comprises at least about half of the total length of needle 40. However, preferably proximal portion 48 comprises the majority of the total length of needle 40 to facilitate blood flow in the annular space formed between needle 40 and catheter 20. Needle 40 defines a lumen 46 therein. Lumen 46 can extend completely through needle 40 or through only distal portion 49. Preferably, lumen 46 is occluded so no fluid flows out of the proximal end of needle 40. Even more preferably, lumen 46 extends only through distal portion 49. See FIG. 2a.

Needle 40 should include a notch 42 formed therein. Alternatively, a series of notches 42 and 43 may be used. See FIG. 2. Notches 42 and 43 should be located in distal portion 49. Notches 42 and 43 allow blood to flow therethrough and into the annular space between needle 40 and catheter 20. This allows the clinician to observe flashback of blood along a distal location of catheter 20 if catheter 20 is translucent or transparent. Preferably, notch 42 is located at the transition or juncture between distal portion 49 and proximal portion 48. See FIGS. 3, 5, 7 and 9. The location of notch 42 here serves two useful purposes. First, notch 42 defines an opening having a portion that is parallel to the path of blood flow through lumen 46. This facilitates egress of blood outside of needle 40. Second, the annular space between proximal portion 48 and catheter 20 is larger than the annular space between distal portion 49 and catheter 20. Thus, by having notch 42 at the transition between proximal portion 48 and distal portion 49, blood can easily flow out of needle 40 and flow through the annular space between proximal portion 48 and catheter 20. And the larger volume makes blood visualization easier for the clinician. Furthermore, this increased blood volume will easily travel from this annular space through extension tube 50 where it can be observed by the clinician through a window 27. Notch 42 should have a cross-sectional area that is equal to or greater than the cross-sectional area of the annular space formed between proximal portion 48 and catheter 20.

Figure 5:
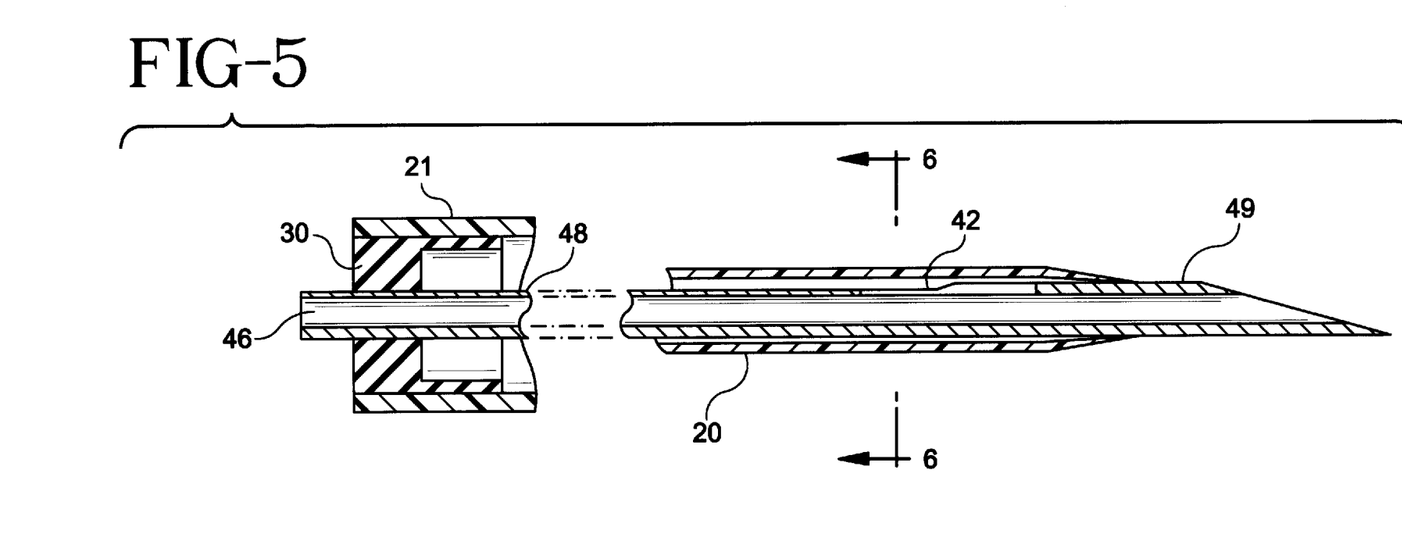
FIG. 5 is an enlarged cross-sectional view of still another embodiment of the needle and elastic plug of this invention.
Figure 6:
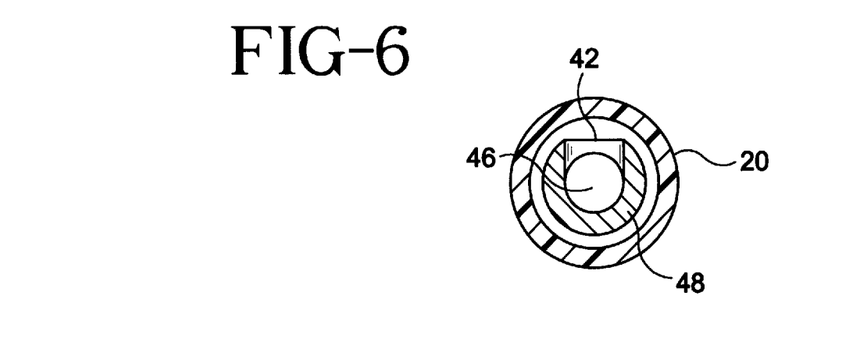
FIG. 6 is a cross-sectional view taken along line 6—6 of FIG. 5.
Figure 7:
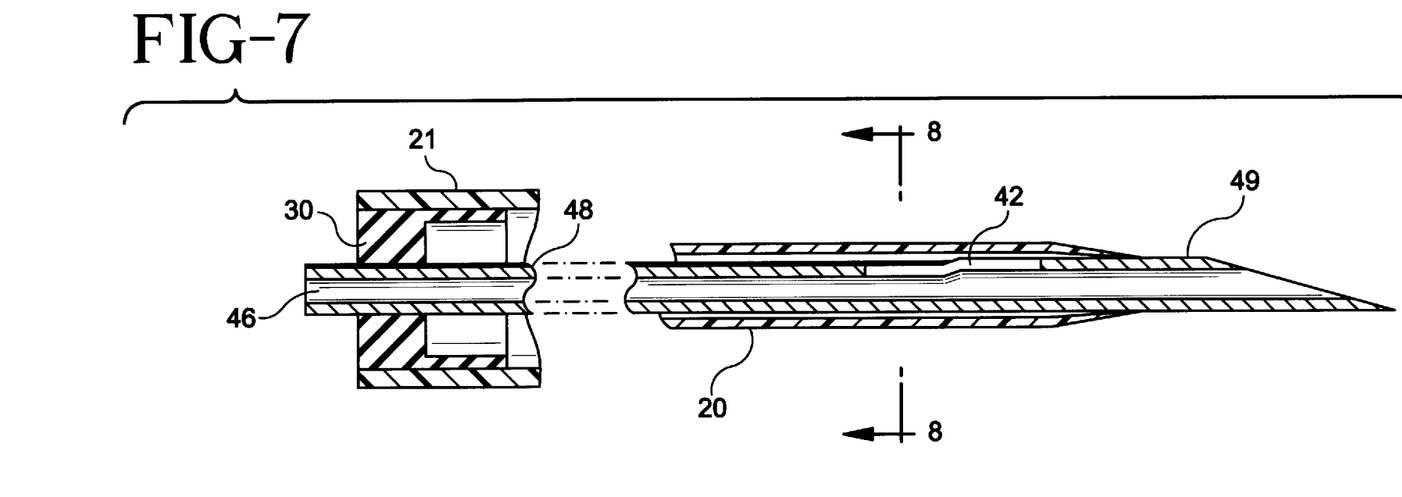
FIG. 7 is an enlarged cross-sectional view of yet another embodiment of the needle and elastic plug of this invention.

Proximal portion 48 can be formed with a different cross-section as compared to distal portion 49 by any standard method. For example, proximal portion 48 can be stamped, ground or swaged. FIGS. 3, 4, 7, 8 and 10 show proximal portion 48 which has been formed by stamping. FIGS. 5 and 6 show proximal portion 48 which has been formed by grinding. In addition, needle 40 could be initially formed with the proximal portion 48 having a different cross-section than distal portion 49.

When needle 40 is inserted completely into catheter 20 in the forward most position so that needle hub 41 is engaged with catheter hub 21, the distal tip of needle 40 extends beyond the distal tip of catheter 20. The distal tip of catheter 20 tightly grips distal portion 49 of needle 40 to aid insertion of the catheter into the patient and to resist peelback of the catheter. This also provides an effective fluid seal at the distal end of the assembly. An elastic plug 30 located proximal of notch 42 in catheter hub 21 provides a proximal fluid seal. This arrangement prevents blood leakage from the interior of catheter 20 since blood is trapped between elastic plug 30 and the distal tip of catheter 20 and can only exit through extension tube 50.

Elastic plug 30 is formed from an elastomeric material to define a solid cylinder. Polyisoprene or latex could be used to form elastic plug 30. Preferably, polyisoprene is used. Elastic plug 30 may or may not be held in radial compression by catheter hub 21. Elastic plug 30 is preferably radially compressed approximately 10% to 40%, preferably 15%, so that the outside diameter of elastic plug 30 is reduced approximately to the dimension of the inner diameter of catheter hub 21. This compression of elastic plug 30 may be simultaneous along the length thereof or may be gradual, beginning at one end and continuing to the other. Thus, catheter hub 21 securely retains elastic plug 30 in a state of radial compression where elastic plug 30 defines a diameter equal to approximately 85% of its initial non-compressed diameter.

Figure 9:
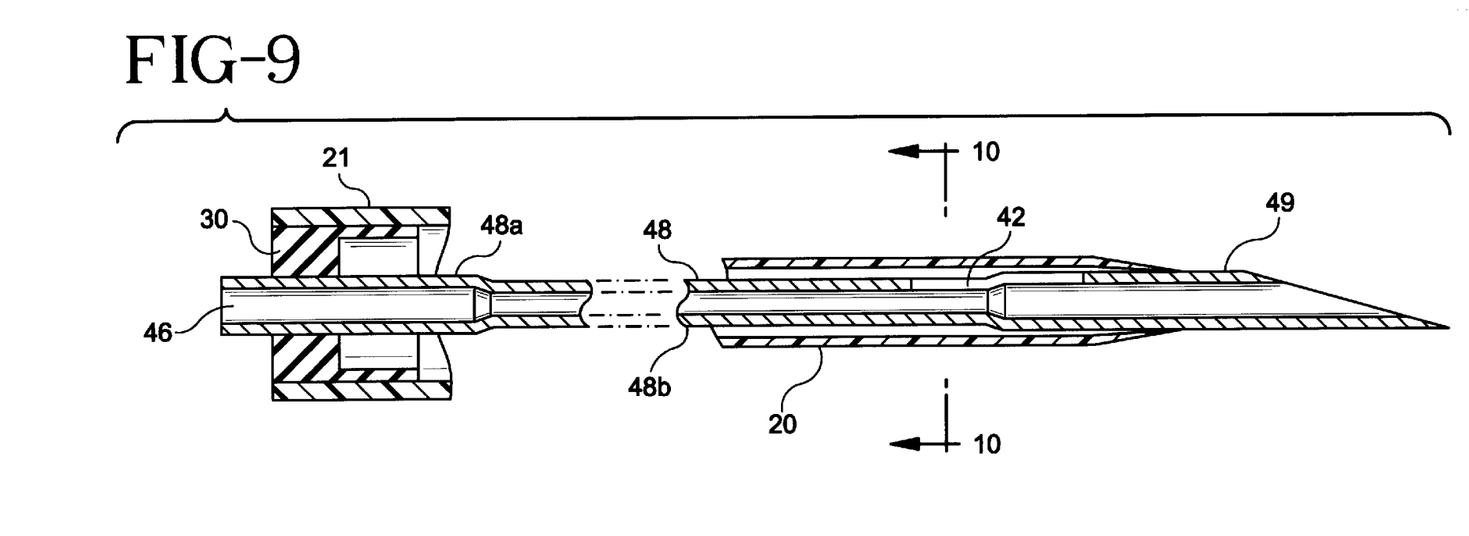
FIG. 9 is an enlarged cross-sectional view of a further embodiment of the needle and elastic plug of this invention.

With needle 40 located in catheter 20 such that the distal tip of needle 40 is located distal of the distal tip of catheter 20, proximal portion 48 resides in elastic plug 30. Needle 40 may remain in this position for a lengthy period of time in the inventory of a hospital or other medical institution until such time as the catheter and introducer needle are needed. However, once catheter 20 has been inserted into a patient and needle 40 has been removed from elastic plug 30 and catheter 20, the elastic material of elastic plug 30 returns toward an unbiased condition such that the space that had been occupied by needle 40 is substantially filled. Where proximal portion 48 has a reduced cross-section as compared to distal portion 49 and resides in elastic plug 30, only a smaller aperture must be closed. Thus sealing of elastic plug 30 after removal of needle 10 is facilitated by the radial compression of elastic plug 30 and the smaller aperture left by proximal portion 48 in elastic plug 30. Although it is preferable for proximal portion 48 to have a reduced cross-section as compared to distal portion 49 and for proximal portion 48 to reside in elastic plug 30, it is not critical that this occur. For example, as seen in FIG. 9, proximal portion 48 could include a proximal section 48a that has a cross-section the same as or comparable to that of distal section 49. In addition, proximal portion 48 could include an intermediate section 48b that has a reduced cross-section as compared to distal portion 49.

Thus, it is seen that the use of a multiple cross-section needle in conjunction with an elastic plug inhibits the elastic material of the plug from taking a permanent set to the needle, even when the needle has been in the elastic plug for a considerable time, and completely fills the space that had been occupied by the needle. This prevents blood leakage and avoids microbial infection to the patient. In addition, the combination of the needle notch and the proximal portion of the needle having a different cross-section than the distal portion of the needle provides sufficient blood flow in the annular space between the needle and the catheter to provide the clinician with a clear indication, adjacent to the distal end of the assembly, that a venipuncture has been successful.

We claim:

1. A medical device comprising:
   a generally tubular member having opposed inner and outer surfaces and a selected internal cross-sectional dimension;
   an elastic plug having an outer surface and being disposed in the generally tubular member with the outer surface of the plug being in abutting face-to-face relationship with the inner surface of the generally tubular member; and
   a needle with a proximal end and having a proximal portion with a first cross-section and a distal portion with a second cross-section larger than the first cross-section of the proximal portion and a juncture between the proximal portion and the distal portion and wherein the proximal portion resides in the plug and wherein the needle defines a lumen therein and a notch in fluid communication with the lumen and the notch is located at the juncture between the proximal portion and the distal portion.

2. The medical device of claim 1 wherein the lumen does not extend completely through the needle.

3. A medical device comprising:
   a generally tubular member having opposed inner and outer surfaces and a selected internal cross-sectional dimension;
   an elastic plug having an outer surface and being disposed in the generally tubular member with the outer surface of the plug being in abutting face-to-face relationship with the inner surface of the generally tubular member wherein the elastic plug is compressible and, which in an uncompressed condition, defines an outer cross-sectional dimension greater than the internal cross-sectional dimension of the generally tubular member, and wherein the plug is radially compressed by the generally tubular member; and
   a needle with a proximal end and having a proximal portion with a first cross-section and a distal portion with a second cross-section larger than the first cross-section of the proximal portion and a juncture between the proximal portion and the distal portion and wherein the proximal portion resides in the plug and wherein the needle defines a lumen therein and a notch in fluid communication with the lumen and the notch is located at the juncture between the proximal portion and the distal portion.

4. The medical device of claim 3 wherein the lumen does not extend completely through the needle.

5. A catheter, comprising:
   a cannula having a proximal end and a distal end;
   a hub connected to the proximal end of the cannula; and
   an introducer needle disposed in the cannula having a distal end, a distal portion with a first cross-section, a proximal portion with a second cross-section different than the first cross-section, a juncture between the distal portion and the proximal portion, and a proximal end, the needle including a lumen disposed in the needle and a notch in fluid communication with the lumen wherein the notch is located at the juncture between the proximal portion and the distal portion.

6. The catheter of claim 5 wherein the lumen does not extend completely through the needle.

7. A catheter comprising:
   a cannula having a proximal end and a distal end;
   a hub connected to the proximal end of the cannula; and
   an introducer needle disposed in the cannula having a distal end, a distal portion with a first cross-section, a proximal portion with a second cross-section different than the first cross-section, wherein the first cross-section is larger than the second cross-section, a juncture between the distal portion and the proximal portion, and a proximal end, the needle including a lumen disposed in the needle and a notch in fluid communication with the lumen wherein the notch is located at the juncture between the proximal portion and the distal portion.

8. The catheter of claim 7 wherein the lumen does not extend completely through the needle.

9. A catheter comprising:

a cannula having a proximal end and a distal end;

a hub connected to the proximal end of the cannula;

an elastic plug disposed in the hub; and an introducer needle disposed in the cannula having a distal end, a distal portion with a first cross-section, an intermediate portion with a second cross-section, wherein the second cross-section is different than the first cross-section, a juncture between the distal portion and the intermediate portion, a proximal portion with a third cross-section and a proximal end wherein the proximal portion resides in the elastic plug and wherein the needle includes a lumen and a notch and the notch is located at a juncture between the distal portion and the intermediate portion.

10. The catheter of claim 9 wherein the lumen does not extend through the needle.

* * * * *